US009299330B2

(12) United States Patent
Shi (10) Patent No.: US 9,299,330 B2
(45) Date of Patent: Mar. 29, 2016

(54) APPARATUS AND METHOD TO ENHANCE THE EXPRESSIVE QUALITIES OF DIGITAL MUSIC

(71) Applicant: Zheng Shi, Beijing (CN)

(72) Inventor: Zheng Shi, Beijing (CN)

(*) Notice: Subject to any disclaimer, the term of this patent is extended or adjusted under 35 U.S.C. 154(b) by 0 days.

(21) Appl. No.: 14/737,514

(22) Filed: Jun. 12, 2015

(65) Prior Publication Data

US 2015/0279343 A1 Oct. 1, 2015

Related U.S. Application Data

(63) Continuation-in-part of application No. PCT/CN2015/070162, filed on Jan. 6, 2015, which is a continuation-in-part of application No. PCT/CN2014/080317, filed on Jun. 19, 2004, which is a continuation-in-part of application No. PCT/CN2014/079891, filed on Jun. 13, 2014, said application No. PCT/CN2015/070162 is a continuation-in-part of application No. PCT/CN2014/090890, filed on Nov. 12, 2014, which is a continuation-in-part of application No. PCT/CN2014/080495, filed on Jun. 23, 2014, which is a continuation-in-part of application No. PCT/CN2014/079892, filed on Jun. 13, 2014, which is a continuation-in-part of application No. PCT/CN2014/072961, filed on Mar. 6, 2014, which is a continuation-in-part of application No. PCT/CN2014/071850, filed on Jan. 30, 2014, said application No. PCT/CN2015/070162 is a continuation-in-part of application No. PCT/CN2014/091918, filed on Nov. 21, 2014.

(51) Int. Cl.
*G10H 1/18* (2006.01)
*G10H 1/055* (2006.01)

(52) U.S. Cl.
CPC ............. *G10H 1/18* (2013.01); *G10H 1/0551* (2013.01); *G10H 2220/275* (2013.01); *G10H 2220/461* (2013.01)

(58) Field of Classification Search
USPC .................................................. 84/615, 733
IPC ............................................................ G10H 1/18
See application file for complete search history.

(56) References Cited

U.S. PATENT DOCUMENTS

| | | | | |
|---|---|---|---|---|
| 3,979,990 | A * | 9/1976 | Hinago | 84/719 |
| 4,213,367 | A * | 7/1980 | Moog | 84/689 |
| 4,615,252 | A * | 10/1986 | Yamauchi et al. | 84/687 |
| 5,025,705 | A * | 6/1991 | Raskin | 84/743 |
| 5,107,748 | A * | 4/1992 | Muramatsu et al. | 84/658 |
| 5,453,571 | A * | 9/1995 | Adachi et al. | 84/658 |
| 5,495,074 | A * | 2/1996 | Kondo et al. | 84/690 |
| 6,362,412 | B1 * | 3/2002 | Ura | 84/658 |
| 6,384,305 | B1 * | 5/2002 | Lee | 84/21 |
| 6,472,589 | B1 * | 10/2002 | Lee | 84/21 |
| 6,501,011 | B2 * | 12/2002 | Wesley | 84/719 |
| 7,408,108 | B2 * | 8/2008 | Ludwig | 84/719 |
| 7,538,268 | B2 * | 5/2009 | Marcus | 84/723 |
| 8,797,288 | B2 * | 8/2014 | Zaliva | 345/173 |
| 9,019,237 | B2 * | 4/2015 | Ludwig et al. | 345/175 |

(Continued)

*Primary Examiner* — David Warren (57) ABSTRACT

The present invention disclosed an apparatus and method for capturing directly the dynamic motion of a finger to create digital music with enhanced expressive qualities through the use of a capacitance sensor that is configured to continuously produce an analog output of capacitance change upon the approaching but not yet touching, touching and leaving the key or space between keys by a finger.

12 Claims, 8 Drawing Sheets

(56) References Cited

U.S. PATENT DOCUMENTS

| | | | |
|---|---|---|---|
| 2005/0034590 A1* | 2/2005 | Querfurth | 84/645 |
| 2008/0141847 A1* | 6/2008 | Komatsu et al. | 84/440 |
| 2011/0132182 A1* | 6/2011 | Kikumoto | 84/744 |
| 2011/0167993 A1* | 7/2011 | Lan et al. | 84/744 |
| 2013/0205972 A1* | 8/2013 | Osuga et al. | 84/433 |
| 2013/0205973 A1* | 8/2013 | Osuga et al. | 84/433 |
| 2013/0205974 A1* | 8/2013 | Osuga et al. | 84/433 |
| 2014/0083281 A1* | 3/2014 | McPherson et al. | 84/615 |
| 2015/0075355 A1* | 3/2015 | Chui et al. | 84/609 |

\* cited by examiner

APPARATUS AND METHOD TO ENHANCE THE EXPRESSIVE QUALITIES OF DIGITAL MUSIC

CROSS-REFERENCE TO RELATED APPLICATION

This application is a continuation in part of International Patent Application No. PCT/CN2015/070162, entitled "Apparatus and Method to Enhance the Expressive Qualities of Digital Music", filed on Jan. 6, 2015, which is a continuation in part of International Patent Application No. PCT/CN2014/080317, entitled "System and Method for Learning, Composing, and Playing Music with Physical Objects", filed on Jun. 19, 2014, which is a continuation in part of International Patent Application No. PCT/CN2014/079891, entitled "System and Method for Operating a Computer Program with Physical Objects", filed on Jun. 13, 2014.

International Patent Application No. PCT/CN2015/070162 is also a continuation in part of International Patent Application No. PCT/CN2014/090890, entitled "System and Method for Recognizing Objects with Continuous Capacitance Sensing", filed on Nov. 12, 2014, which is a continuation in part of International Patent Application No. PCT/CN2014/080495, entitled "System and Method to Recognize an Object's ID, Orientation and Location Relative to an Interactive Surface", filed on Jun. 23, 2014, which is a continuation in part of International Patent Application No. PCT/CN2014/079892, entitled "System and Method for Identifying an Object's ID and Location Relative to an Interactive Surface", filed on Jun. 13, 2014, which is a continuation of International Patent Application No. PCT/CN2014/072961, entitled "System and Method for Identifying an Object's ID and Location Relative to an Interactive Board", filed on Mar. 6, 2014, which is a continuation in part to International Patent Application No. PCT/CN2014/071850, entitled "System and Method for Identifying an Object's ID and Location Relative to an Interactive Board", filed on Jan. 30, 2014.

International Patent Application No. PCT/CN2015/070162 is also a continuation in part of International Patent Application No. PCT/CN2014/091918, entitled "System and Method for Changing the State of User Interface Element Marked on Physical Objects", filed on Nov. 21, 2014.

The entire disclosures of each of the above applications are incorporated herein by reference.

TECHNICAL FIELD

The present invention relates to digital musical instruments. More specifically, the present invention relates to a digital musical instrument that produces music with enhanced expressive qualities.

BACKGROUND

An acoustic instrument produces sound and music that originates from the material, structure and artisanship of the instrument itself. An acoustic instrument, in the hands of an experienced player, can create sound and music with high expressive qualities, in terms of texture, timbre, articulation and dynamics in the music parlance, or in terms of their expressed nuance, sophistication, emotion or even inspiration as appreciated by those who love music.

On the other hand, a digital instrument produces sound and music that are retrieved and synthesized from a digital library of sound and music. Despite decades of efforts, a digital instrument has not been able to retain much of the expressive qualities of an acoustic instrument. It is certainly true that music created by digital instruments can be enhanced with many effects. For example, MIDI data can be used to add digital effects to the sounds played, such as reverb, chorus, delay and tremolo. However, a button may still need to be pushed each time an effect is to be activated or deactivated. These "effects" cannot match the expressive qualities created by a professional with an acoustic instrument, when various techniques can be employed at once and at will to express the interpretation of the music by the professional. For example, it is therefore difficult to allow a vibrato or a portamento at once and at will, when an electronic piano is played in the violin mode.

To enhance the expressive qualities of a digital keyboard instrument, one approach has been to place 2, 3 or even more sensors under each key. The velocity of the key depressions are captured and corrected in complex ways to produce a sound of the key that incorporates the speed and force of the key depression. Most of the time a direct proportional relationship between the velocity and the amplitude of the note is adopted. The enhancement of expressive quality of this approach is still fundamentally limited by the number of data points being collected for each key depression action.

People have also sought to increase the amount of data points being collected by using different kind of sensors. Hall-effect sensor, photoelectric sensor, piezoelectric sensor, or pressure sensor have all been tried to generate a more continuous or analogue output that captures better the dynamics of a single keystroke by a person. In all of these efforts, the result of the key movements generate by a figure touch action is captured with finer granularity, but the dynamic movement of the finger itself is not directly captured. One limitation is that no prior art to date has been able to capture the motion of a finger when the finger is approaching or leaving the key but is actually not touching the key. Another limitation is that no prior art to date has been able to capture the motion of a finger when the finger is touching a space between the physical boundaries of two sensors. With most digital keyboards marketed with the functionality to play a myriad of instrument sound including piano and stringed instruments, these limitations produces some loss of musical expressions when the keyboard is played as a keyboard instrument, and severe loss of musical expressions when the keyboard is played as a stringed instrument. Moreover, these limitations do not help to enable a digital instrument to become even more seamlessly expressive than an acoustic instrument.

Simply put, a seamless integration of producing a note through touching a key or a string and making the note expressive through a variety of techniques comes very naturally for an acoustic instrument; nonetheless, such seamless integration is yet to be enabled for a digital instrument, with one barrier being the inability of prior art to capture the dynamics and sophistication of the finger motion directly. Therefore, there is a need to capture directly the unique dynamics of the touch action by an experienced player of the musical instrument, so as to enable a digital instrument to generate a music piece that is as seamlessly expressive as an acoustic instrument.

SUMMARY OF INVENTION

The present invention disclosed an apparatus and method for capturing directly the dynamic motion of a touch action by a finger to create digital music with enhanced expressive qualities.

In accordance with one embodiment of the present invention, an apparatus for generating music is disclosed, which comprises a board with an array of keys wherein each key is associated with a music note, a processor, memory, a program which is stored in the memory and configured to be executed by the processor. The apparatus further includes a second memory that records the description of music and replays the music, and a sound module that converts the description of music into sound of music.

In accordance with one embodiment of the present invention, one or more capacitance sensors are placed underneath the surface of each of the keys, wherein each of the capacitance sensors is configured to continuously produce an analogue output of capacitance change upon the occurrence of a touch action rather than exporting an "on" and "off" binary output. Consequently, the capacitance sensor is capable of detecting a touch action including finger approaching but not yet touching the board, finger touching a key on the board with strong force or weak force, finger touching space between keys on the board, and finger leaving the board, which are all beyond a simple contact of a finger on the key.

In accordance with one embodiment of the present invention, upon one or more fingers touch actions with the board, the capacitance sensor is configured to detect the touch actions and produce continuously analogue output of capacitance change. A program stored in the memory and executed by the processor is configured to create a digital profile of the capacitance change of the touch actions. Parameters of the digital profile include distance between the finger and the capacitance sensor, velocity, acceleration, deceleration, force and duration of the finger touch. The program further determines the music playing action such as vibrato or portamento that corresponds to the touch action or a set of touch actions. The program further applies one or more heuristics of the music playing action to convert the digital profile of the touch action or a set of touch actions into a description of music in the Musical Instrument Digital Interface (MIDI) format.

In accordance with one embodiment of the present invention, one or more heuristics include a vibrato heuristic, a portamento heuristic, a key depression heuristic, a legato heuristic, a detache heuristic, a staccato heuristic, a spiccato heuristic, and a harmonic heuristic.

The present invention seamlessly integrates producing a note through touching a key and making the note expressive through a variety of techniques that come very naturally for an acoustic instrument, and enables a digital instrument to generate a music piece that is as seamlessly expressive as an acoustic instrument.

BRIEF DESCRIPTION OF THE DRAWINGS

To better illustrate the technical features of the embodiments of the present invention, various embodiments of the present invention will be briefly described in conjunction with the accompanying drawings. It should be obvious that the drawings are for exemplary embodiments of the present invention, and that a person of ordinary skill in the art may derive additional drawings without deviating from the principles of the present invention.

FIGS. 3A-3D are exemplary schematic diagrams illustrating the touch actions applied to a music apparatus of the present invention, in order to enable the performance of certain music-playing techniques, in accordance with one embodiment of the present invention.

DETAILED DESCRIPTION OF THE INVENTION

While the present invention will be described using specific embodiments, the invention is not limited to these embodiments. People skilled in the art will recognize that the apparatus and method of the present invention may be used in many other applications. The present invention is intended to cover all alternatives, modifications and equivalents within the spirit and scope of invention, which is defined by the apprehended claims.

Furthermore, in the detailed description of the present invention, specific details are set forth in order to provide a thorough understanding of the present invention. However, it will be obvious to one of ordinary skill in the art that the present invention may be practiced without these specific details. For example, the term Musical Instrument Digital Interface (MIDI) is discussed in this present invention as an example technology and for the purpose of simplicity; however, other digital music technologies and formats can also be adapted and adopted for the purpose of this present invention and are within the scope of the present invention. Another example is the use of the term keyboard in this present invention that serves as an example format of the musical instrument being enabled by this present invention; however, other musical instrument formats can also be adapted, adopted or created for the purpose of this present invention and are within the scope of the present invention. Yet another example is the use of the capacitance sensor technology in this present invention; however, other sensor technology can also be adapted, adopted or created for the purpose of this present invention and are within the scope of the present invention.

In other instances, well known methods, procedures, components, and circuits are not described in details to avoid unnecessarily obscuring a clear understanding of the present invention.

The present invention may be better understood and its numerous objects and advantages will become apparent to those skilled in the art by reference to the accompanying drawings.

Figure 1:
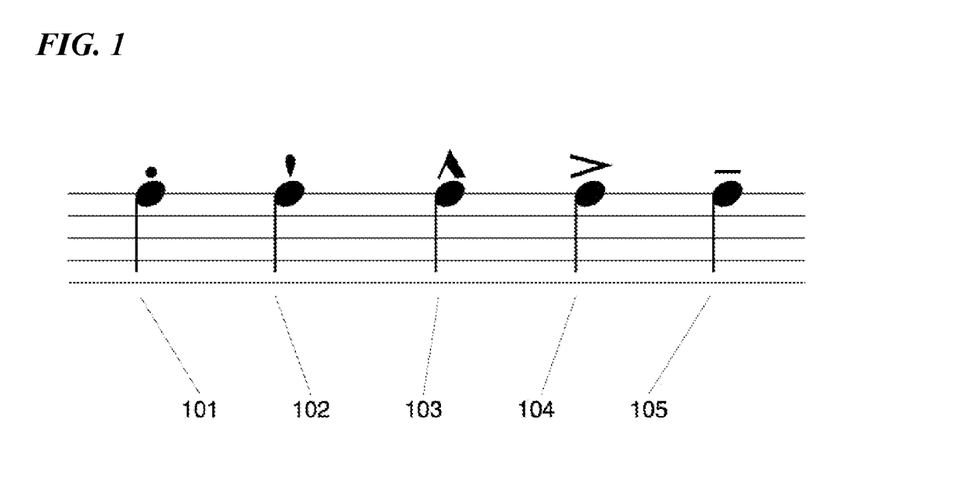
FIG. 1 is an exemplary schematic diagram illustrating certain music articulation techniques for a stringed instrument that are difficult to perform by a digital musical instrument of the prior art.

FIG. 1 is an exemplary schematic diagram illustrating certain music articulation techniques for a stringed instrument that are difficult to perform by a digital musical instrument of the prior art.

As shown in FIG. 1, five examples of music articulation techniques for a stringed instrument are referenced, from left to right, i.e., staccato (101), staccatissimo (102), martellato (103), marcato (104), and tenuto (105). All of the music articulation techniques are difficult to be distinguished by a digital keyboard instrument.

In addition, other expressive qualities such as vibrato, tremolo, portamento and harmonic are generally difficult to be performed seamlessly on a digital musical instrument. In a performance, these techniques may require the assistance of a pitch-bend wheel, a sustain pedal, a modulation wheel; alternatively, they may require the performer to switch mode of digital instrument on the fly.

Figure 2:
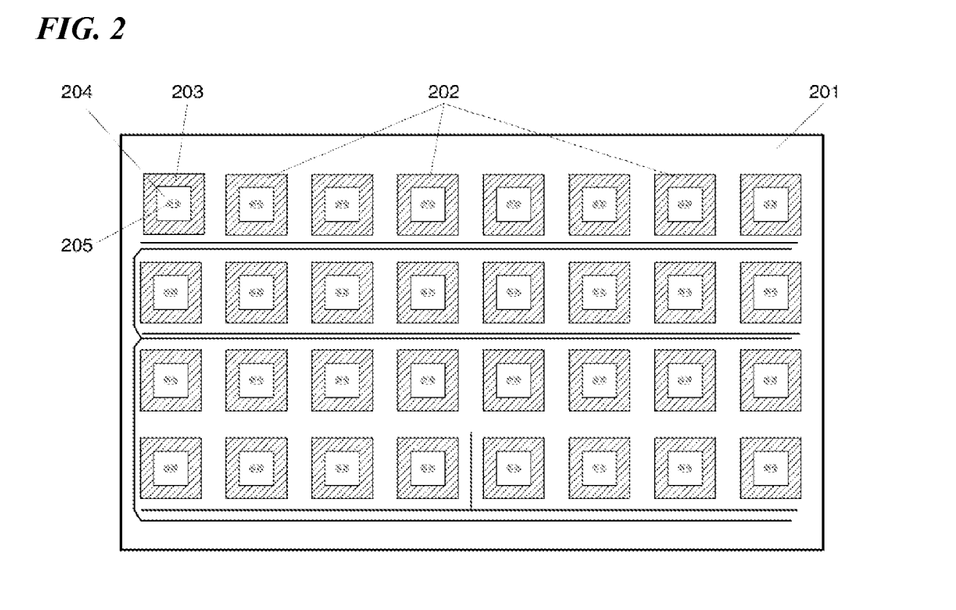
FIG. 2 is an exemplary schematic diagram illustrating an array of self-capacitance sensors in accordance with one embodiment of the present invention.

FIG. 2 is an exemplary schematic diagram illustrating an array of self-capacitance sensors in accordance with one embodiment of the present invention.

As shown in FIG. 2, the capacitance sensor array 201 includes a total of 32 self-capacitance sensors 202. Each self-capacitance sensor 202 includes a metallic square 203 that is one electrode of the self-capacitance sensor 202 and an LED light 205 placed at the center of an empty square 204 that is placed at the center of the metallic square 203, as a sensory device for an end-user. The capacitance sensor array 201 further includes a microprocessor (not shown in FIG. 2) that is connected to all 32 sensors.

Once one or more self-capacitance sensors 202 are placed underneath the surface of a key, each of the capacitance sensors 202 is configured to continuously produce an analogue output of capacitance change upon the occurrence of a touch action on the keyboard rather than exporting an "on" and "off" binary output. The touch action can be finger approaching but not yet touching the board, finger touching a key on the board with strong force or weak force, finger touching space between keys on the board, and finger leaving the board. Finger touching the board can be finger touching a key, finger touching the area around a key, or finger touching the area between two or more keys.

FIGS. 3A-3D are exemplary schematic diagrams illustrating the touch actions applied to a music apparatus of the present invention, in order to enable the performance of certain music-playing techniques, in accordance with one embodiment of the present invention.

As shown in FIGS. 3A-3D, three keys 302, 303 and 304 among an array of keys placed on the board 301 are used. The middle key 302 is the N key, and the keys adjacent to the N key 302 are the N−1 key 303 on the left and N+1 key 304 on the right. An N−1, N and N+1 capacitance sensors are placed underneath the surface of the N−1 key 303, N key 302 and N+1 key 304, respectively.

Figure 3A:
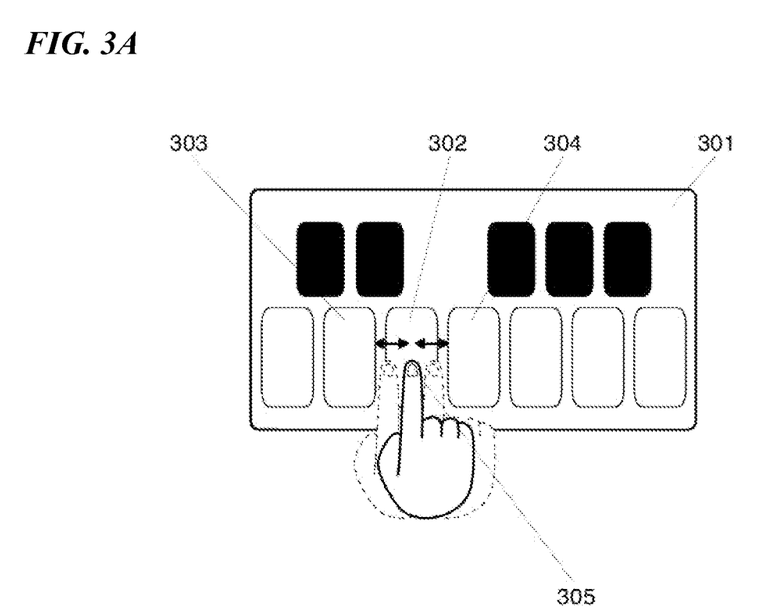
FIG. 3A is an exemplary schematic diagram illustrating a vibrato action performed on a music apparatus of the present invention that simulates a vibrato action performed on a stringed musical instrument, in accordance with one embodiment of the present invention.

FIG. 3A is an exemplary schematic diagram illustrating a vibrato action performed on a music apparatus of the present invention that simulates a vibrato action performed on a stringed musical instrument, in accordance with one embodiment of the present invention. In this embodiment of the present invention, a vibrato action is achieved by placing a finger 305 upon the N key 302, and then moving the finger 305 to the left and then right in a rhythmic fashion without the finger 305 leaving the board and without fully reaching either the N−1 key 303 or the N+1 key 304. In other words, it is a finger gesture that very much resembles the vibrato technique for an acoustic stringed instrument.

Figure 3B:
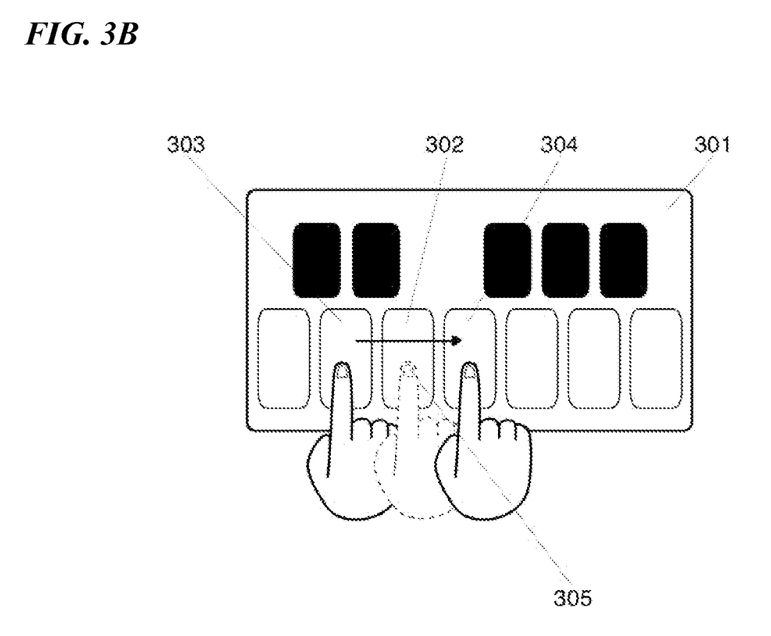
FIG. 3B is an exemplary schematic diagram illustrating a portamento action performed on a music apparatus of the present invention that simulates a portamento action performed on a stringed musical instrument, in accordance with one embodiment of the present invention.

FIG. 3B is an exemplary schematic diagram illustrating a portamento action performed on a music apparatus of the present invention that simulates a portamento action performed on a stringed musical instrument, in accordance with one embodiment of the present invention. In this embodiment of the present invention, a portamento action is achieved by placing a finger 305 upon the N−1 key 303, and then moving the finger 305 to the right, passing the N key 302 and reaching the N+1 key 304, in a smooth sliding motion, without the finger 305 leaving the board. In other words, it is a finger gesture that very much resembles the portamento technique for an acoustic stringed instrument.

Figure 3C:
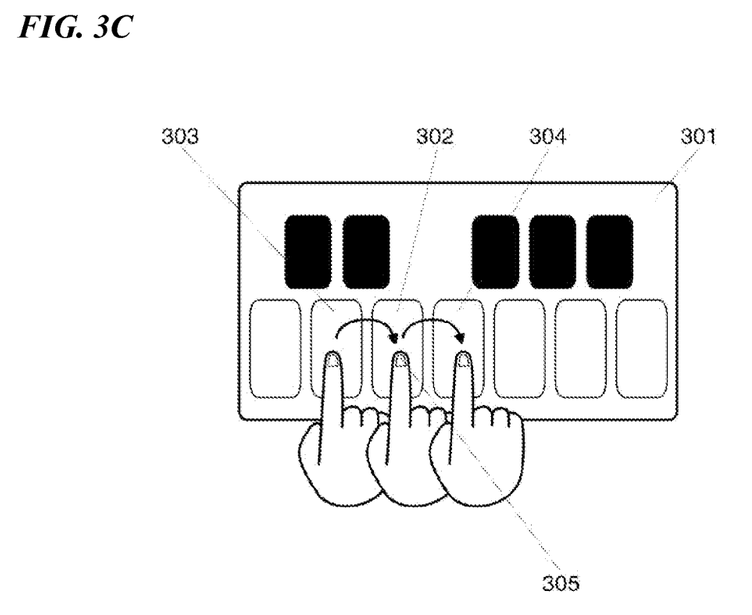
FIG. 3C is an exemplary schematic diagram illustrating a legato action performed on a music apparatus of the present invention that simulates a legato action performed on a stringed musical instrument, in accordance with one embodiment of the present invention.

FIG. 3C is an exemplary schematic diagram illustrating a legato action performed on a music apparatus of the present invention that simulates a legato action performed on a stringed musical instrument, in accordance with one embodiment of the present invention. In this embodiment of the present invention, a legato action is achieved by placing a finger 305 upon the N−1 key 303, and then moving the finger 305 to the N key 302, and then moving the finger 305 to the N+1 key 305, in a smooth motion, while lifting the finger 305 slightly up from the board in a "low jump" fashion in between the keys.

Figure 3D:
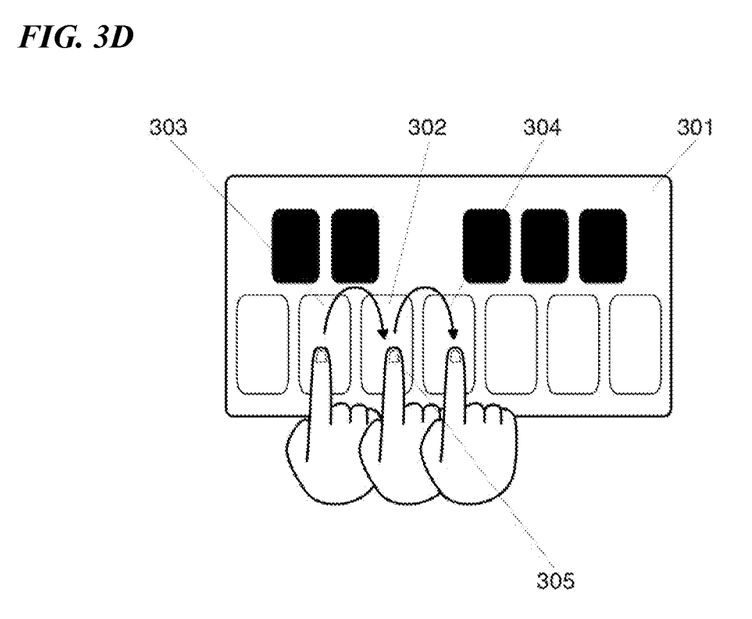
FIG. 3D is an exemplary schematic diagram illustrating a staccato action performed on a music apparatus of the present invention that simulates a staccato action performed on a stringed musical instrument, in accordance with one embodiment of the present invention.

FIG. 3D is an exemplary schematic diagram illustrating a staccato action performed on a music apparatus of the present invention that simulates a staccato action performed on a stringed musical instrument, in accordance with one embodiment of the present invention. In this embodiment of the present invention, a staccato action is achieved by a finger 305 approaching, touching and leaving the N−1 sensor 303 quickly and forcefully, then the finger 305 approaching, touching and leaving the N sensor 302 quickly and forcefully, then the finger 305 approaching, touching and leaving the N+1 sensor 304 quickly and forcefully. Each time after the touching action is completed, the finger 305 is lifted completely away from the board in a "high jump" fashion in between the keys.

Figure 4:
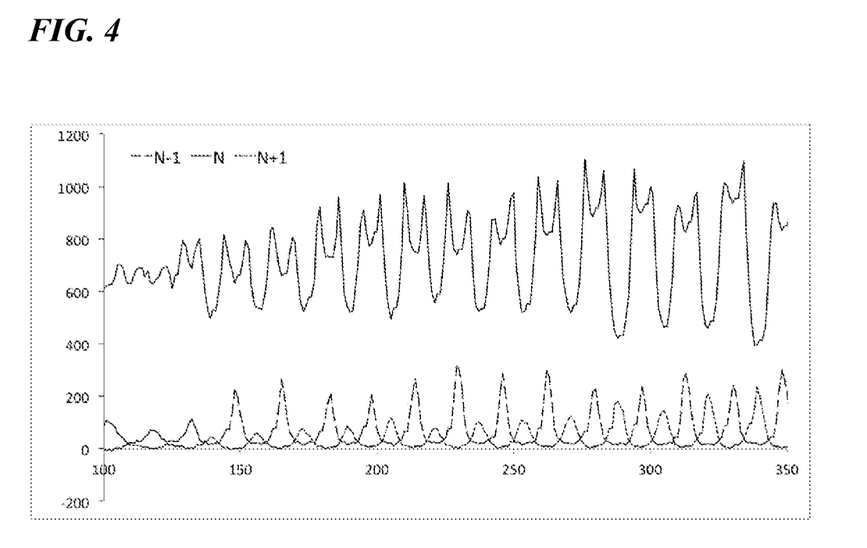
FIG. 4 is an exemplary schematic graphic illustrating the analogue outputs of three capacitance sensors embedded in a music apparatus of the present invention that captures a vibrato action illustrated in FIG. 3A, in accordance with one embodiment of the present invention.

FIG. 4 is an exemplary schematic graphic illustrating the analogue outputs of three capacitance sensors embedded in a music apparatus of the present invention that captures a vibrato action illustrated in FIG. 3A, in accordance with one embodiment of the present invention.

This pattern of movement is a direct simulation of the vibrato action for a stringed instrument, such as a violin or viola, and its characteristics are captured by the output of capacitance of the three sensors shown in the graphic in FIG. 4.

The N−1, N, and N+1 curves represent the capacitance output of the N−1 sensor, the N sensor, and the N+1 sensor, respectively. The x-axis is time and y-axis is analogue value of capacitance. The vibrato action illustrated in FIG. 3A generates a pattern whereby the N−1 curve reaches a small peak, followed by the N curve reaching a large peak, followed the N+1 curve reaching a small peak, followed by the N curve reaching a large peak, followed by the N−1 curve reaching a small peak, and so on and so forth.

In accordance with one embodiment of the present invention, a program stored in the memory and executed by the processor is configured to create a digital profile of the capacitance change of the touch actions, determine music playing action of the touch actions to be a vibrato action for a stringed musical instrument, and apply a vibrato heuristic to convert the digital profile into a description of a vibrato action in the Musical Instrument Digital Interface (MIDI) format.

The characteristics of the digital profile of the three curves include the peak value of the capacitance, the velocity and acceleration and deceleration of capacitance changes, the duration that the capacitance stays at peak value, and the time for each change to complete one cycle. The description of a vibrato action is described by the main pitch, the volume of the note, and the rate, depth and delay of the vibrato.

The conversion of the characteristics of the digital profile of the curves of capacitance change into description of music in the MIDI format is illustrated below:
  the main pitch of the note is the pitch associate with the N sensor that has produced the largest capacitance output value throughout the time period;
  the volume of the note is determined by the velocity by which the capacitance output of the N sensor reaches a peak value, and by the actual peak value of the capacitance output of the N sensor;
  the rate of the vibrato is determined by the duration of each of the cycles of capacitance changes for all three capacitance curves;
  the depth of the vibrato is determined by the amplitude of the N−1 curve and the N+1 curve relative to the amplitude of the N curve;
  the delay of the vibrato is set to be as long as this particular pattern of movement is in motion.

As such, in the case of a vibrato action, the dynamic motion of a finger upon a key is captured directly, and a description of the music in MIDI format is generated seamlessly, through no other action than what a skilled music instrument player would otherwise do on an acoustic instrument.

Figure 5:
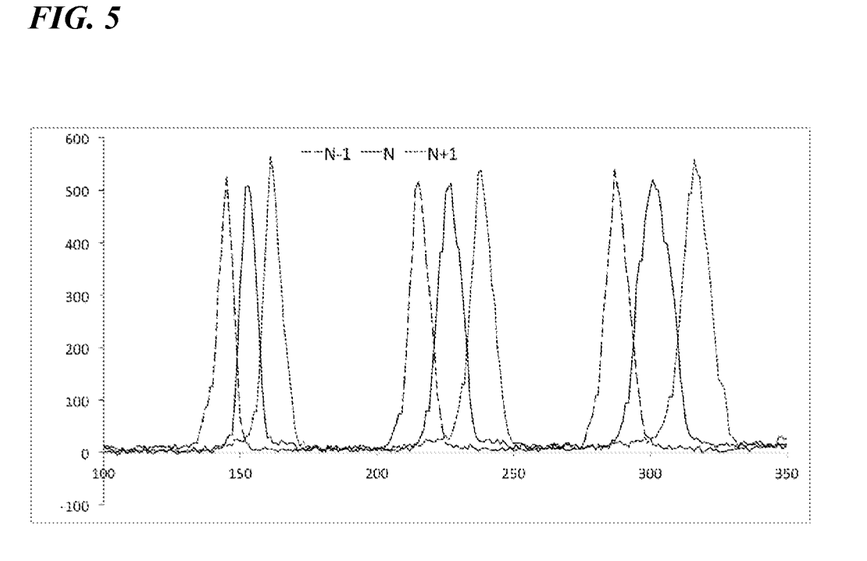
FIG. 5 is an exemplary schematic graphic illustrating the analogue outputs of three capacitance sensors embedded in a music apparatus of the present invention that captures a portamento action illustrated in FIG. 3B, in accordance with one embodiment of the present invention.

FIG. 5 is an exemplary schematic graphic illustrating the analogue outputs of three capacitance sensors embedded in a music apparatus of the present invention that captures a portamento action illustrated in FIG. 3B, in accordance with one embodiment of the present invention.

This pattern of movement is a direct simulation of the portamento action for a stringed instrument, such as a violin or viola, and its characteristics are captured by the output of capacitance of the three sensors shown in the graphic in FIG. 5.

Similarly to FIG. 4, the N−1, N and N+1 curves represent the capacitance output of the N−1 sensor, the N sensor, and the N+1 sensor, respectively. The x-axis is time and y-axis is analogue value of capacitance. The portamento action illustrated in FIG. 3B generates a pattern whereby the N−1 curve reaches a peak, followed by the N curve reaching a peak while the N−1 curve still maintains a substantial value, followed by the N+1 curve reaching a peak while the N curve still maintains substantial value.

In accordance with one embodiment of the present invention, a program stored in the memory and executed by the processor is configured to create a digital profile of the capacitance change of the touch actions, determine music playing action of the touch actions to be a portamento action for a stringed musical instrument, and apply a portamento heuristic to convert the digital profile into a description of a portamento action in the Musical Instrument Digital Interface (MIDI) format.

The characteristics of the digital profile of the three curves, and the conversion of these characteristics into description of music in the MIDI format, are illustrated below:
  the starting pitch of the portamento is the pitch associate with the N−1 sensor;
  the ending pitch of the portamento is the pitch associate with the N+1 sensor;
  the interim pitch between the starting pitch and the ending pitch at any point in the middle of the portamento is a pitch assigned based on a calculation considering the relative value of capacitance of the two adjacent sensors at that point, based on a number of mathematical algorithms. The simplest mathematical algorithm is to assign an interim pitch at a point in between the N−1 to N sensor, based on the physical distances of the point to the N−1 sensor and the N sensor. The physical distances can be further derived by measuring the capacitance sensed by the N−1 sensor and the N sensor, as the finger moves from the N−1 sensor to the N sensor while maintaining contact with the board, and by constructing a calibration curve based on the resulting capacitance data over distance;
  the volume of the portamento is determined by the velocity by which the capacitance output reaches a peak value, and by the actual peak value, of each of the N−1, N and N+1 curves respectively;
  the rate of the portamento is determined by the duration of each of the cycles of capacitance changes for all three capacitance curves.

As such, in the case of a portamento action, the dynamic motion of a finger upon a key is captured directly, and a description of the music in MIDI format is generated seamlessly, through no other action than what a skilled music instrument player would otherwise do on an acoustic instrument.

More generically, this embodiment of the present invention allows a digital keyboard instrument that has discrete pitches associated with the discrete set of keys to be played like a digital stringed instrument that produces gradual and continuous pitch changes as the finger slides through the keys.

Figure 6:
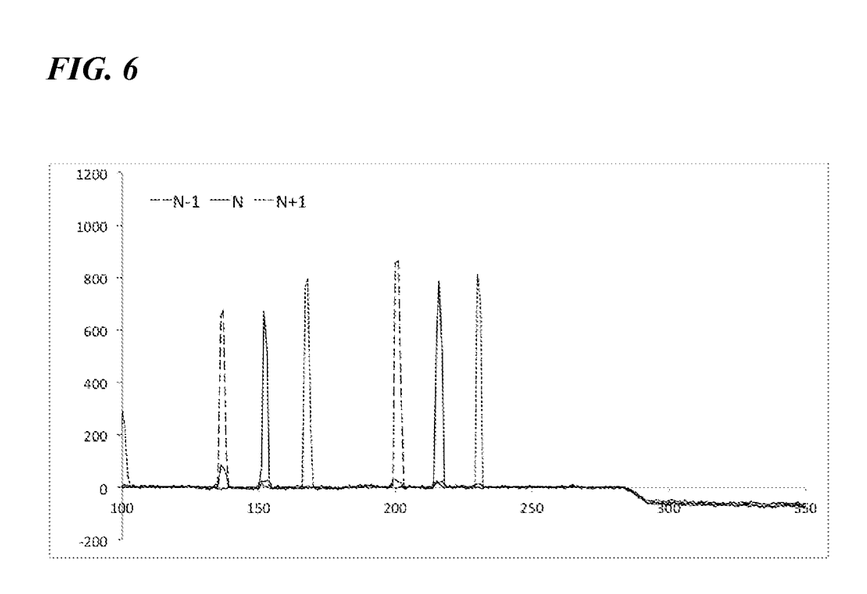
FIG. 6 is an exemplary schematic graphic illustrating the analogue outputs of three capacitance sensors embedded in a music apparatus of the present invention that captures a staccato action illustrated in FIG. 3D, in accordance with one embodiment of the present invention.

FIG. 6 is an exemplary schematic graphic illustrating the analogue outputs of three capacitance sensors embedded in a music apparatus of the present invention that captures a staccato action illustrated in FIG. 3D, in accordance with one embodiment of the present invention.

This pattern of movement is a direct simulation of the staccato action for a stringed instrument, such as a violin or viola, and its characteristics are captured by the output of capacitance of the three sensors shown in the graphic in FIG. 6.

Similarly to FIG. 5, the N−1, N, and N+1 curves represent the capacitance output of the N−1 sensor, the N sensor, and the N+1 sensor, respectively. The x-axis is time and y-axis is analogue value of capacitance.

In accordance with one embodiment of the present invention, a program stored in the memory and executed by the processor is configured to create a digital profile of the capacitance change of the touch actions, determine music playing action of the touch actions to be a staccato action for a stringed musical instrument, and apply a staccato heuristic to convert the digital profile into a description of a staccato action in the Musical Instrument Digital Interface (MIDI) format.

The characteristics of the digital profile of the three curves and the corresponding conversion to MIDI description are self-explanatory. The digital profile of a staccato action is illustrated here to serve as a contrast to the digital profile of the portamento action.

Figure 7:
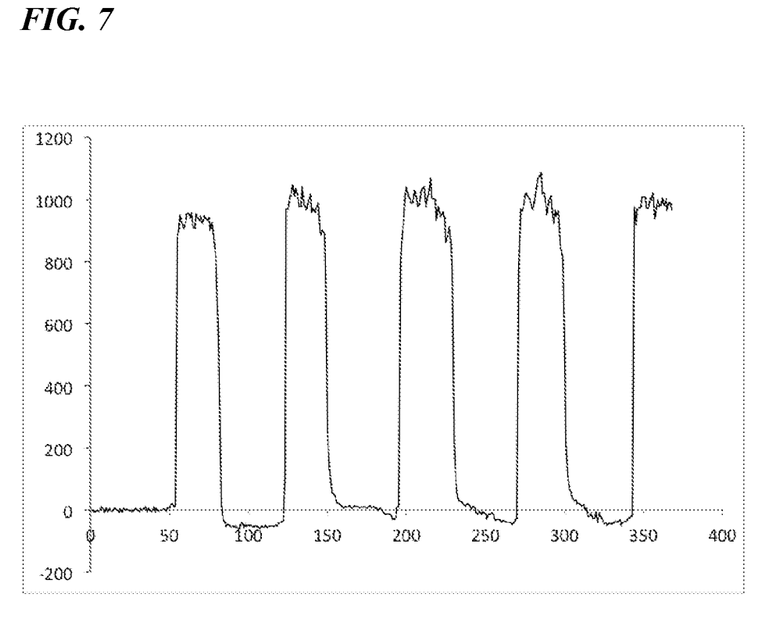
FIG. 7 is an exemplary schematic graphic illustrating the analogue outputs from a single capacitance sensor embedded in a music apparatus of the present invention that captures a strong and fast key depression action performed on a music apparatus of the present invention that simulates a strong and fast key depression action performed on a keyboard musical instrument, in accordance with one embodiment of the present invention.

FIG. 7 is an exemplary schematic graphic illustrating the analogue outputs from a single capacitance sensor embedded in a music apparatus of the present invention that captures a strong and fast key depression action performed on a music apparatus of the present invention that simulates a strong and fast key depression action performed on a keyboard musical instrument, in accordance with one embodiment of the present invention.

The characteristics of a strong and fast key depression action for a keyboard instrument are captured by the output of capacitance of the sensor shown in the graphic in FIG. 7. The x-axis is time and y-axis is analogue value of capacitance.

In accordance with one embodiment of the present invention, a program stored in the memory and executed by the processor is configured to create a digital profile of the capacitance change of the touch actions, determine music playing action of the touch actions to be a strong and fast key depression action for a keyboard musical instrument, and apply a key depression heuristic to convert the digital profile into a description of a strong and fast key depression action in the Musical Instrument Digital Interface (MIDI) format.

The characteristics of the digital profile of the curve, and the conversion of these characteristics into description of music in the MIDI format, are illustrated below:
  the pitch of the key depression is the pitch associated with the sensor;
  the initial volume of the key depression is determined by the velocity by which the capacitance output reaches a threshold value;
  a series of after touch messages are further generated, as the capacitance output further increases, to raise the volume of the key depression;
  a sustain message is further generated, as the capacitance output stays at the maximal value for a duration;
  the volume decreases as the capacitance output decreases in value, and reaches zero as the capacitance output falls below the threshold value.

As such, in the case of a strong and fast key depression action, the dynamic motion of a finger upon a key is captured directly, and a description of the music in MIDI format is generated seamlessly, through no other action than what a skilled music instrument player would otherwise do on an acoustic instrument, and without the assistance of a sustain pedal.

Figure 8:
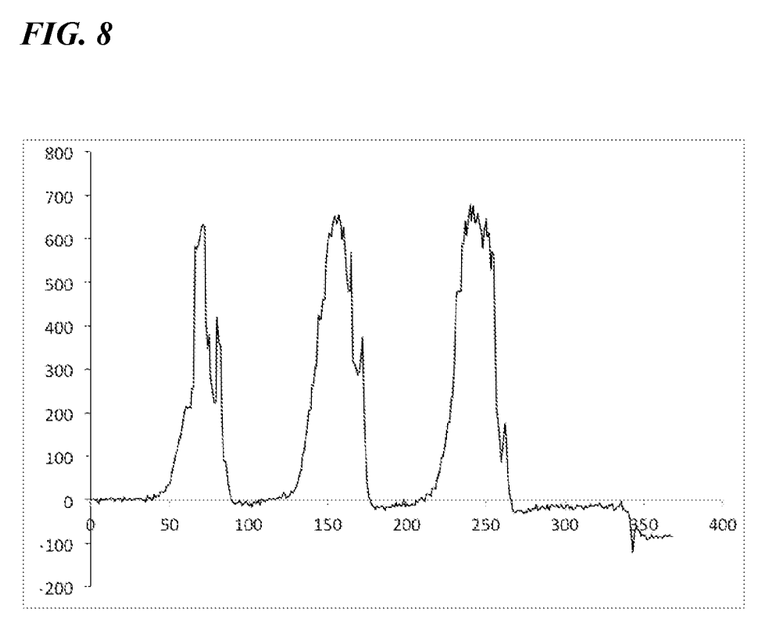
FIG. 8 is an exemplary schematic graphic illustrating the analogue outputs from a single capacitance sensor embedded in a music apparatus of the present invention that captures a soft and slow key depression action performed on a music apparatus of the present invention that simulates a soft and slow key depression action performed on a keyboard musical instrument, in accordance with one embodiment of the present invention.

FIG. 8 is an exemplary schematic graphic illustrating the analogue outputs from a single capacitance sensor embedded in a music apparatus of the present invention that captures a soft and slow key depression action performed on a music apparatus of the present invention that simulates a soft and slow key depression action performed on a keyboard musical instrument, in accordance with one embodiment of the present invention.

The characteristics of a soft and slow key depression action for a keyboard instrument are captured by the output of capacitance of the sensor shown in the graphic in FIG. 8. The x-axis is time and y-axis is analogue value of capacitance.

In accordance with one embodiment of the present invention, a program stored in the memory and executed by the processor is configured to create a digital profile of the capacitance change of the touch actions, determine music playing action of the touch actions to be a soft and slow key depression action for a keyboard musical instrument, and apply a key depression heuristic to convert the digital profile into a description of a soft and slow key depression action in the Musical Instrument Digital Interface (MIDI) format.

The characteristics of the digital profile of the curve, and the conversion of these characteristics into description of music in the MIDI format, are illustrated below:
  the pitch of the key depression is the pitch associated with the sensor;
  the initial volume of the key depression is determined by the velocity by which the capacitance output reaches a threshold value;
  a series of after touch messages are further generated, as the capacitance output further increases, to raise the volume of the key depression;
  a sustain message is further generated, as the capacitance output stays at the maximal value for a duration;
  the volume decreases as the capacitance output decreases in value, and reaches zero as the capacitance output falls below the threshold value.

It should be noted that, in contrast to the graph in FIG. 7, the capacitance output curve in FIG. 8 takes longer to ramp up to maximal value and still longer to decline to baseline value. The capacitance output curve in FIG. 8 also reaches a lower peak value than the curve in FIG. 7. These characteristics are all consistent with the key depression action illustrated in FIG. 8 being softer and slower than the key depression action illustrated in FIG. 7.

The descriptions in the proceeding paragraphs from FIG. 4 to FIG. 8 illustrate various embodiments of the present invention wherein a music playing action, such as vibrato (FIG. 4), portamento (FIG. 5), staccato (FIG. 6), a strong and fast key depression (FIG. 7) and a soft and slow key depression (FIG. 8), is captured by the apparatus or the method of the present invention. In other embodiments of the present invention, music playing actions such as a legato action, a detache action, a spiccato action, and a harmonic action are captured and converted into descriptions of music in the MIDI format, wherein the corresponding touch actions are substantially similar to those finger actions when playing an acoustic musical instrument.

In accordance with one embodiment of the present invention, a soft and sustained finger touch action upon a key is detected by a capacitance sensor, and a program generates a digital profile of the touch action, determines the music playing action of the touch action to be a harmonic action, and converts the digital profile into a description of harmonics with the note associated with key being the root of the harmonic, by applying a harmonics heuristics to the digital profile.

Figure 9:
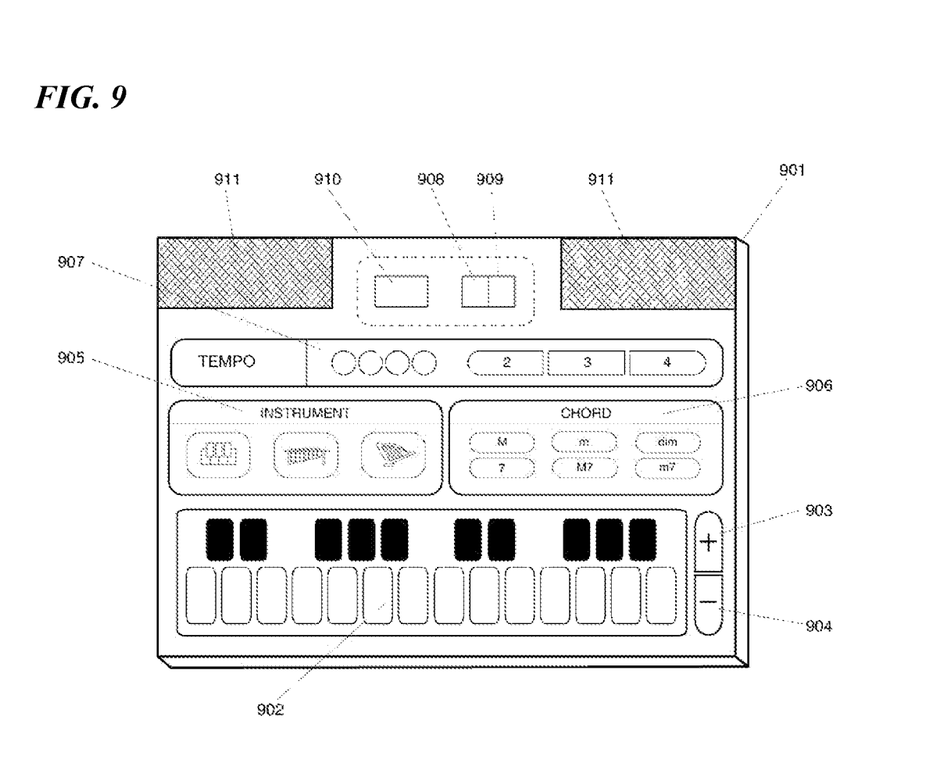
FIG. 9 is an exemplary schematic diagram of an apparatus for generating music with enhanced expressive qualities, in accordance with one embodiment of the present invention.

FIG. 9 is an exemplary schematic diagram of an apparatus for generating music with enhanced expressive qualities, in accordance with one embodiment of the present invention.

As shown in FIG. 9, the apparatus 901 includes a keyboard 902 with an array of keys, each associated with a music note, and two buttons 903 and 904 with a plus and a minus symbol whose function is to raise or lower the pitch of the entire keyboard by a single octave. One or more capacitance sensors are placed underneath the surface of each of the keys of the keyboard 902, and each of the capacitance sensors is configured to be capable of continuously producing an analogue output of capacitance change upon the occurrence of a touch action. The apparatus 901 further includes a musical instrument selection section 905 to allow for choices of the types of musical instrument to be simulated, a chord section 906 to allow the keyboard to generate, instead of a single note, a chord with the associated note being the root, and a tempo section 907 to allow the tempo to be set for the music being generated.

The apparatus 901 is further embedded with a processor 908, a memory 909, a sound module 910, and a pair of speakers 911. Stored in the memory 909 is a program that is configured to be executed by the processor 908. After the capacitance sensors detect one or more finger touch actions with the board and produce analogue output of capacitance change during the entire duration of the touch actions, the program applies one or more heuristics to the one or more finger touch actions to create a digital profile of the touch actions, and to convert the digital profile into a description of music in the Musical Instrument Digital Interface (MIDI) format. The sound module 910 is for converting the description of music in the MIDI format into sound of music.

In accordance with one embodiment of the present invention, the digital profiles of the one or more touch actions and the description of music derived from the digital profiles are stored in a memory 909 for future replay.

Figure 10:
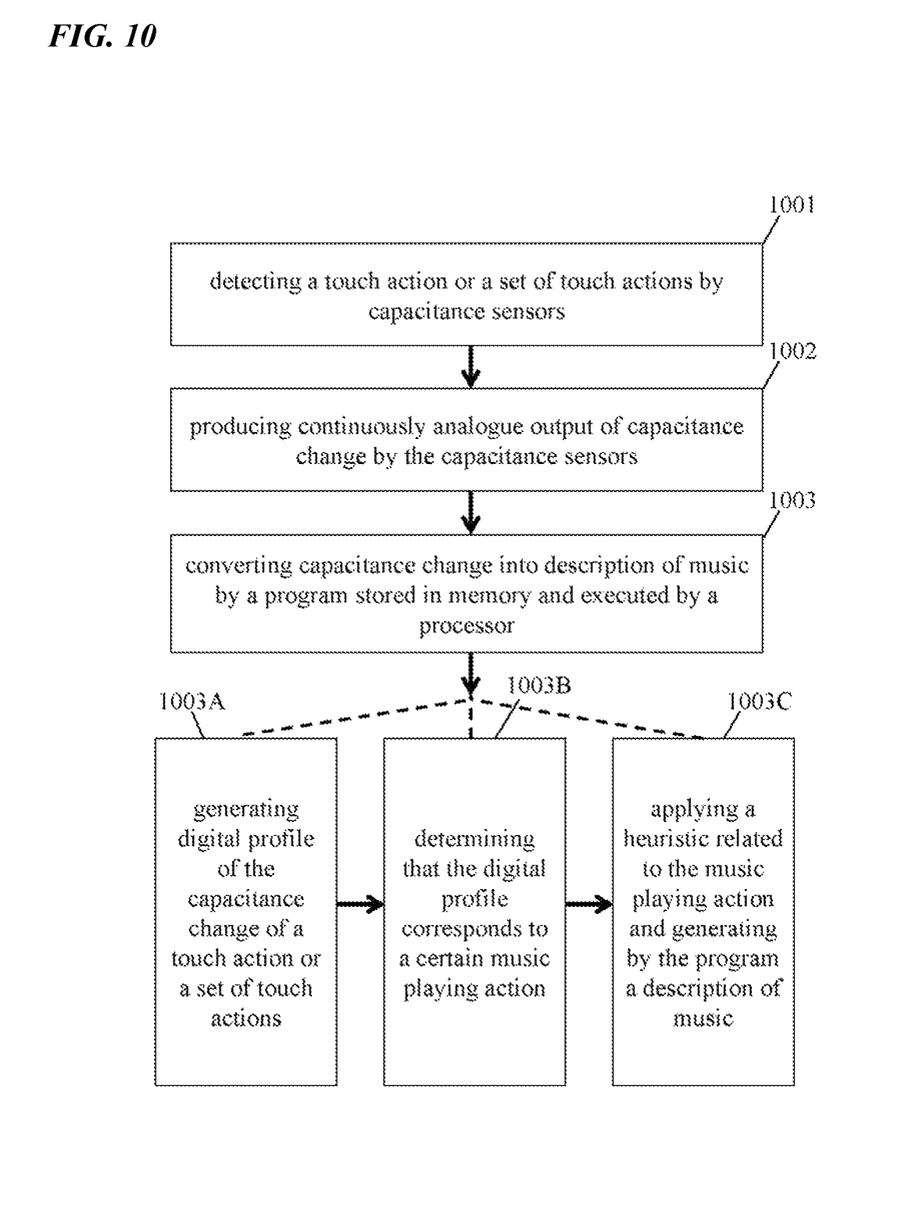
FIG. 10 is an exemplary schematic diagram of a method for generating music with enhanced expressive qualities, in accordance with one embodiment of the present invention.

FIG. 10 is an exemplary schematic diagram of a method for generating music with enhanced expressive qualities, in accordance with one embodiment of the present invention. As shown in FIG. 10, the method includes the following steps:

At a board with an array of keys and each key is associated with a music note,

Step 1001: detecting a touch action or a set of touch actions by capacitance sensors. The detection is achieved once the capacitance change caused by a finger and sensed by a capacitance sensor placed underneath the surface of each of the keys exceeds a threshold value, or a multiple of the threshold value.

Step 1002: producing continuously analogue output of capacitance change by capacitance sensors. As long as the capacitance change exceeds a threshold value, the capacitance sensor is configured to continue sense and output analogue value of capacitance change.

Step 1003: converting capacitance change into description of music by a program stored in memory and executed by processor. Converting, by a program stored in memory and executed by a processor, the capacitance change of the touch action or a set of touch actions into a description of music in the Musical Instrument Digital Interface (MIDI) format:

Step 1003A: generating digital profile of the capacitance change of a touch action or a set of touch actions. Generating by the program a digital profile of the capacitance change of a touch action or a set of touch actions, wherein the digital profile comprises a parameter selected from a group consisting of distance, velocity, acceleration, deceleration, force and duration;

Step 1003B: determining that the digital profile corresponds to a certain music playing action. Determining by the program that the digital profile corresponds to a certain music playing action, such as a vibrato or a portamento;

Step 1003C: applying a heuristic related to the music playing action and generating by the program a description of music.

The invention claimed is:

1. An apparatus for generating music, comprising
   a board with an array of keys and each key is associated with a music note,
   a capacitance sensor placed underneath the surface of each of the keys,
   a processor,
   memory,
   a program stored in the memory and configured to be executed by the processor,
   wherein each of the capacitance sensors is configured to detect a touch action by a finger and to continuously produce analogue output of capacitance change for the duration of the touch action,
   wherein the program is configured to generate a digital profile of the capacitance change of a touch action or a set of touch actions, and wherein the digital profile comprises a parameter selected from a group consisting of distance, velocity, acceleration, deceleration, force and duration,
   wherein the program is configured to determine that the digital profile corresponds to a certain music playing action,
   and wherein the program is configured to apply one or more heuristics related to the music playing action and generate a description of music.

2. The apparatus in claim 1, wherein the one or more heuristics comprise,
   a vibrato heuristic for determining that a finger is touching a key with a primarily lateral movement that moves back and forth from a center position of the key in a rhythmic fashion while maintaining contact with the board, and for describing the touch actions as a vibrato action for a stringed musical instrument,
   a portamento heuristic for determining that a finger has touched a first key and is moving laterally towards a second key while maintaining contact with the board, and for describing the touch actions as a portamento action for a stringed musical instrument.

3. The apparatus in claim 2, wherein the vibrato action is captured by three neighboring sensors, a first sensor, a second sensor that is left to the first sensor, and a third sensor that is right to the first sensor, and wherein the vibrato heuristic further comprises;
   a main pitch of a note is the pitch associated with the first sensor that has produced the largest capacitance output value throughout a time period;
   a volume of the note is determined by the velocity by which the capacitance output of the first sensor reaches a peak value, and by the actual peak value of the capacitance output of the first sensor;
   a rate of the vibrato action is determined by the duration of each of the cycles of capacitance changes for capacitance curves of the three sensors;
   a depth of the vibrato action is determined by the amplitude of the capacitance curves of the second sensor and the third sensor relative to the amplitude of the capacitance curve of the first sensor;
   a delay of the vibrato action is set to be as long as the particular pattern of movement is in motion.

4. The apparatus in claim 2, wherein the portamento action is captured by three neighboring sensors, a fourth sensor, a fifth sensor that is left to the fourth sensor, and a sixth sensor that is right to the fourth sensor, and wherein the portamento heuristic further comprises a starting pitch of the portamento action is the pitch associated with the fifth sensor;

a ending pitch of the portamento action is the pitch associated with the sixth sensor;

an interim pitch between the starting pitch and the ending pitch at any point in the middle of the portamento action is a pitch assigned based on a calculation considering the relative value of capacitance of the fifth sensor and the sixth sensor at that point;

a volume of the portamento action is determined by the velocity by which the capacitance output reaches a peak value, and by the actual peak value, of each of the capacitance curves of the three sensors respectively;

a rate of the portamento action is determined by the duration of each of the cycles of capacitance changes for capacitance curves of the three capacitance curves.

5. The apparatus in claim 1, wherein the one or more heuristics comprise, a key depression heuristic for determining that a finger is touching a key with a primarily vertical movement that is soft and slow, and for describing the touch actions as soft and slow key depression for a keyboard musical instrument, a key depression heuristic for determining that a finger is touching a key with a primarily vertical movement that is strong and fast, and for describing the touch actions as strong and fast key depression for a keyboard musical instrument.

6. The apparatus in claim 1, wherein the one or more heuristics comprise a heuristic selected from a group consisting of a legato heuristic, a detache heuristic, a staccato heuristic, a spiccato heuristic, and a harmonic heuristic.

7. The apparatus in claim 1, wherein the board further comprises one or more keys and each key is associated with a music related element that is selected from a group consisting of a tempo, an accidental, a symbol of dynamics, a symbol of articulation, and a symbol representing a particular type of musical instrument, and that is to be incorporated into a description of music.

8. A method for generating music, comprising at a board with an array of keys and each key is associated with a music note, detecting, by a capacitance sensor placed underneath the surface of each of the keys, a touch action by a finger, producing continuously, by the capacitance sensor, analogue output of capacitance change for the duration of the touch action, generating, by a program stored in memory and executed by a processor, a digital profile of the capacitance change of a touch action or a set of touch actions, wherein the digital profile comprises a parameter selected from a group consisting of distance, velocity, acceleration, deceleration, force and duration, determining by the program that the digital profile corresponds to a certain music playing action, applying by the program one or more heuristics related to the music playing action and generating by the program a description of music.

9. The method in claim 8, wherein the one or more heuristics comprise, a vibrato heuristic for determining that a finger is touching a key with a primarily lateral movement that moves back and forth from a center position of the key in a rhythmic fashion while maintaining contact with the board, and for describing the touch actions as a vibrato action for a stringed musical instrument, a portamento heuristic for determining that a finger has touched a first key and is moving laterally towards a second key while maintaining contact with the board, and for describing the touch actions as a portamento action for a stringed musical instrument.

10. The method in claim 8, wherein the one or more heuristics comprise, a key depression heuristic for determining that a finger is touching a key with a primarily vertical movement that is soft and slow, and for describing the touch actions as soft and slow key depression for a keyboard musical instrument, a key depression heuristic for determining that a finger is touching a key with a primarily vertical movement that is strong and fast, and for describing the touch actions as strong and fast key depression for a keyboard musical instrument.

11. The method in claim 8, wherein the one or more heuristics comprise a heuristic selected from a group consisting of a legato heuristic, a detache heuristic, a staccato heuristic, a spiccato heuristic, and a harmonic heuristic.

12. The method in claim 8, wherein the board further comprises one or more keys and each key is associated with a music related element that is selected from a group consisting of a tempo, an accidental, a symbol of dynamics, a symbol of articulation, and a symbol representing a particular type of musical instrument, and the method further comprising incorporating a music related element associated with a key into a description of music.

\* \* \* \* \*